United States Patent [19]
Linden et al.

[11] Patent Number: 5,634,517
[45] Date of Patent: Jun. 3, 1997

[54] DEVICE FOR REDUCING THE RELATIVE HUMIDITY OF A FLOWING GAS

[75] Inventors: Dan Linden, Stockholm; Magnus Schnuerer, Bromma, both of Sweden

[73] Assignee: Siemens-Elema AB, Solna, Sweden

[21] Appl. No.: 377,262

[22] Filed: Jan. 24, 1995

[30] Foreign Application Priority Data

Jan. 27, 1994 [SE] Sweden ............... 9400253

[51] Int. Cl.⁶ ................ F28B 1/00; F28D 7/12
[52] U.S. Cl. ............. 165/111; 165/142; 55/267; 128/205.12
[58] Field of Search .................. 165/142, 111; 128/205.12, 204.16; 604/319; 55/267; 95/290

[56] References Cited

U.S. PATENT DOCUMENTS

| | | | |
|---|---|---|---|
| 1,458,005 | 6/1923 | Rohrer | 55/267 |
| 3,024,009 | 3/1962 | Booth, Jr. et al. | 165/111 X |
| 3,797,565 | 3/1974 | Fernandes | 165/111 |
| 4,182,129 | 1/1980 | Haunold et al. | 165/142 X |
| 4,230,178 | 10/1980 | Braat et al. | 165/142 X |
| 4,452,303 | 6/1984 | Bontje et al. | 165/142 |
| 4,459,981 | 7/1984 | Mascher et al. | 128/205.12 |
| 4,648,441 | 3/1987 | van de Sluys et al. | 165/111 |
| 4,668,257 | 5/1987 | van der Meer et al. | 55/267 |
| 4,821,737 | 4/1989 | Nelson | |

FOREIGN PATENT DOCUMENTS

| | | |
|---|---|---|
| 0 415 229 | 3/1991 | European Pat. Off. . |
| 0 549 266 | 6/1993 | European Pat. Off. . |
| 1022322 | 1/1989 | Japan ............... 55/267 |
| 455 269 | 7/1988 | Sweden . |
| 1086307 | 4/1984 | U.S.S.R. ............ 55/267 |

OTHER PUBLICATIONS

"Star Exhalation Isolation System Operating Instructions," Siemens Version (Apr. 1988).
"Expired Gas Cooling Device," Attwood et al, Respiratory Care Dept., Methodist Hospital, Indianapolis, IN, Date Unknown.

*Primary Examiner*—Leonard R. Leo
*Attorney, Agent, or Firm*—Hill, Steadman & Simpson

[57] ABSTRACT

A passive device for reducing the relative humidity of a flowing gas has a container in which a tube is disposed. A flowing gas passes into the container through a inlet and then flows downwardly through a cavity in the container, whereupon the gas transfers heat to the tube and the walls of the container. As a result, liquid water condenses from the water vapor content of the gas. The flowing gas then flows upwardly through a channel in the tube and is then warmed by the heat previously transferred to the tube, whereupon the relative humidity of the flowing gas decreases.

14 Claims, 1 Drawing Sheet

5,634,517

DEVICE FOR REDUCING THE RELATIVE HUMIDITY OF A FLOWING GAS

BACKGROUND OF THE INVENTION

1. Field of the Invention

The present invention relates to a device for reducing the relative humidity of a flowing gas which is warmer than an ambient atmosphere, such as gas expired by a live subject of the type having an inlet for the flowing gas, at least one flow-through channel in which the flowing gas is dehumidified and an outlet for the flowing gas.

2. Description of the Prior Art

Dehumidification of a humid flowing gas is important in many contexts. For example, in conjunction with measurement of the flow of flowing gases, many flow meters operate less effectively, and may even produce erroneous measurements, when the flowing gas is so humid that liquid water accumulates in the flow meter by condensation of water vapor. Other measurement instruments, such as various gas analyzers, are also sensitive to condensation inside the measurement instrument. Preventing condensation of water vapor into liquid, which would accordingly affect a measurement instrument, is especially important in the respirator treatment of patients, since the respirator's function is based on correct operation of various measurement instruments. Gas expired by the patient is generally saturated with water vapor and also has a relatively high temperature, about 36° C.

Ambient temperature around the patient where the measurement equipment is located is usually in the range of 18°–22° C. Cooling of expired air is generally unavoidable, and condensation therefore forms.

One known device for dehumidifying air expired by a patient is described in the brochure "Star Exhalation Isolation System Operating Instructions, Siemens Version, Infrasonic Inc., Form No. 9910053, April 1988. The device is connected to the expiratory outlet of a ventilator in order to warm expired gas when it passes through the device. When expired air is warmed, the relative humidity of the expired air decreases thereby reducing the risk of condensation inside a measurement instrument. The reduction of relative humidity occurs because warm air has a higher saturation vapor pressure. One disadvantage of this known device is that it requires an external power source and some type of element for heating the expired air. Moreover, the device must be placed close to the measurement instrument, since the heated gas would otherwise have time to cool again before reaching the measurement instrument.

Another version of a device which reduces the risk of condensation of water vapor in expired air is described in an article entitled "Expired Gas Cooling Device" by J. Attwood and L. Bartel. This device includes a cooling unit for condensing water vapor in expired air before it reaches the measurement instrument. The expired air is cooled in order to reduce the risk of condensation inside the measurement instrument, even if air entering the measurement instrument may still have a very high relative humidity and may even still be saturated. Since a gas with a low temperature cannot hold as much water vapor as a warmer gas, relative humidity as such is not actually reduced when expired air is cooled. There is, however, no additional cooling of the expired air and the risk of condensation inside the measurement instrument is therefore reduced.

The cooling device also requires some external source of power. In this instance, a fan is powered which blows air across a radiator system through which expired gas passes.

In addition to the fact that the described devices stop working when their power source (electric power supply) fails, the devices are also clumsy to use and difficult to clean.

SUMMARY OF THE INVENTION

An object of the present invention is to provide a device of the type initially generally described, which dehumidifies a flowing gas, in particular air expired by a patient, without being subject to the problems described above.

Such a device is achieved in accordance with the principles of the present invention having an element with a through-channel, such as a tube, arranged in a container, with a cavity around the element in the container and the through channel jointly forming the flow-through channel. The inlet is connected to the cavity at one end of the container, the outlet is arranged at one end of the element at the same end of the container, and the other end of the element is at a specific distance from the inlet. The flowing gas passes into the cavity via the inlet, flows along the outside of the element to the through-channel, and passes through same to the outlet.

When, e.g., expired air passes into the cavity in the container via the inlet, the gas passes through the entire element. Since expired gas is warmer than ambient air, some of the heat of the expired gas is transferred to the element. Gas simultaneously cools on the container's inner walls, and water vapor in the flowing gas condenses into liquid on these inner walls. The liquid accumulates in the lowest part of the container. Cooled gas passing into the through channel in the element picks up some of the heat released by the inflowing moist gas to the element. The relative humidity of expired air therefore declines, and the air can pass on to the measurement instrument without any risk of condensation.

For maximum utilization of the thermal effects, it is advantageous if both the element and container have thin walls and are made of a heat-conducting material. Depending on the element's length, however, it could be an advantage if the material's thermal conductivity were not too large. When thermal conductivity is large, there is always a risk of excessively rapid temperature equalization along the element, and heating of the gas flowing toward the outlet would then decline. A material which conducts heat but does not significantly pass it on along the length of the element would be ideal.

It is advantageous to provide the element with a surface area-enlarging exterior, since this will improve heat-extraction from gas flowing in the cavity. One appropriate way to increase the surface area of the element is to provide its exterior with projections.

In the corresponding way, condensation on the inner walls of the container can increase if the container has a surface area-enlarging exterior, since this would increase cooling of the container's walls. In particular, the exterior of the container can be provided with projections, preferably flanges, to form the surface area-enlarging exterior.

It is also an advantage to construct the cavity, element and through-channel so as to have a cylindrical shape.

A cylindrical shape will enable flowing gas to swirl inside the container downwardly toward the through-channel without blocking or impeding the gas flow.

With a cylindrical shape of the element, it is a further advantage to employ a surface area-enlarging projection in the form of a screw-shaped flange facing the cavity. As noted above, this improves the exchange of heat between the downflow of gas in the cavity and the upflow of gas in the through channel.

It is also an advantage to provide the container with a tap hole and to provide a collection vessel connected thereto collect the fluid accumulating due to the condensation of moisture in the flowing gas through the tap hole. The tap hole is preferably devised so the gas flow is not affected by the volume of the collection vessel. For example, a wick or the like could be provided to conduct fluid downwardly into the collection vessel.

The collection vessel is preferably detachably connected so that it can be periodically emptied of water during its use.

In a further embodiment of the invention, the element has at least one additional through-channel.

With an additional through-channel in the element, whereby the respective diameters of the individual channels is preferably reduced, the total heat-conducting surface area is increased, without any increase in the size of the device and without any impediment to gas flow.

Alternatively, the same effect can be achieved by connecting at least one additional element with at least one through-channel in the cavity in the container to form the flow-through channel.

With a plurality of elements, particularly those with a plurality of through-channels, heat conduction and, accordingly, warming of the flowing gas can be optimized.

In another embodiment of the device in accordance with the invention, the element is thermally insulated from the container.

In this way, heat extracted from the gas by the element will not be conducted to the walls of the container at the point of outlet attachment. At the same time, cooling of the container in relation to the surroundings will be more effective, and this will lead, in turn, to increased condensation of moisture in inflowing gas.

DESCRIPTION OF THE PREFERRED EMBODIMENTS

Figure 1:
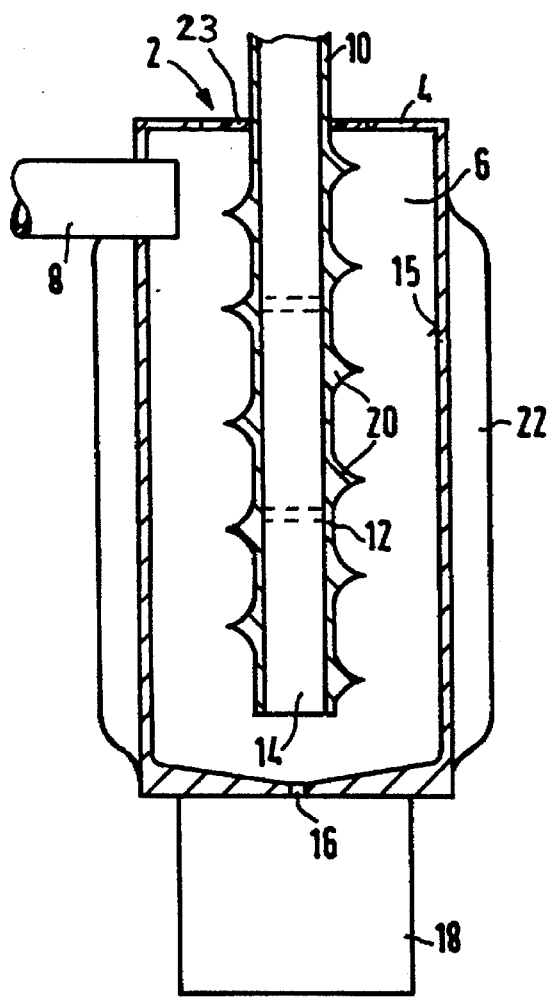
FIG. 1 is a side view, partly in section, of a device, for reducing the relative humidity of a flowing gas, constructed in accordance with the principles of the present invention.

FIG. 1 shows a device 2 for dehumidifying a flowing gas and reducing the risk of condensation in sensitive measurement instruments located downstream from the device 2. The device 2 has a container 4 with a cavity 6. The flowing gas passes into the cavity 6 via an inlet 8. From the container 4, the flowing gas then exits through an outlet 10. A tube 12, thermally insulated from the walls of the container 4, is disposed in the container 4. The tube 12 has a through-channel 14 which connects the outlet 10 to the cavity 6. The flowing gas flows into the cavity 6 via the inlet 8 and continues downwardly through the cavity 6, in contact with both the exterior of the tube 12 and the wall 15 of the container 4 for the entirety of its passage time. If the device 2 is primarily intended for use in conjunction with the ventilation of a patient, the flowing gas consists of warm, expired air which is saturated with moisture. The warm air warms the tube 12 during its passage downwardly through the cavity 6 and loses some of its heat. Heat is also lost to the walls 15 of the container 4. Liquid water thus accumulates in the cavity 6 when water vapor (or minute droplets) in the air condenses. Condensation takes place especially on the walls 15 of the container 4. The condensed moisture runs downwardly to the bottom of the container 4 where it passes through a tap hole 16 into a collection vessel 18 which is detachably mounted on the container 4.

When the somewhat cooled air reaches the bottom of the container 4, it flows upwardly through the through channel 14 in the tube 12. When the gas flows upwardly through the channel 14, it comes into contact with warmer surroundings and is therefore warmed slightly, thereby reducing the relative humidity of the gas. When the gas emerges from the outlet 10, it therefore has a lower temperature and a lower relative humidity, and the risk of condensation inside a measurement instrument downstream from the device 2 is therefore reduced.

Figure 2:
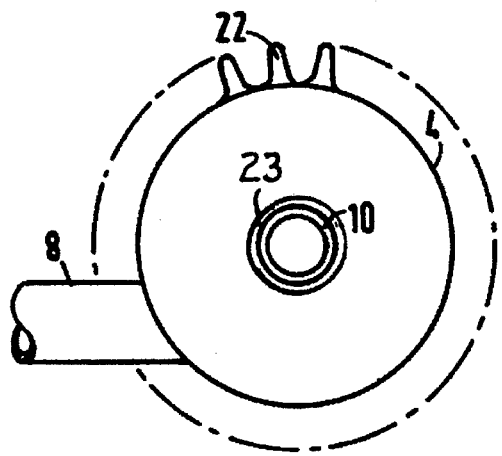
FIG. 2 shows a view of the device of FIG. 1 from above.

As can be seen in FIG. 2, the inlet 8 is eccentrically attached to the container 4, thereby facilitating the flow of gas down through the cavity 6 around the tube 12.

In order to improve the exchange of heat between the gas and the tube 12, the tube 12 is equipped with a screw-like flange 20 extending along its longitudinal direction. The screw-like flange 20 increases the heat-absorbing surface for the passing gas flow. The screw-like flange 20, however, does not impede the flowing gas. Quite the contrary, this design facilitates through flow and reduces turbulence and the mixing of portions of the gas in the cavity 6 respectively having different temperatures and/or relative humidities produced by the action of the device.

The tube 12 should be suitably made from a suitable material with moderate thermal conductivity. Heat in the gas flowing in through the inlet 8 is to be extracted by the tube 12 but is not to be conducted axially along the tube 12, as this would reduce the warming effect when the gas flows toward the outlet 10. In principle, the tube 12 can be devised in sections which are thermally insulated from each other to prevent axial conduction of heat, as schematically indicated by dashed lines.

A ring of thermally insulating material 23 can be provided around the location at which the outlet 10 exits the container 4 in order to avoid thermal transfer between the container 4 and the outlet 10.

The container 4 can also be supplied with external flanges 22 in order to increase the heat-emitting surface area of the container 4. This means that the walls 15 retain the ambient temperature even when large flows of gas pass through the inlet 8.

Alternative designs of the device are also possible. For example, the screw-like flange 20 and the flanges 22 can be excluded completely with no impairment in the basic function of the device 2. The container 4, the tube 12 and the channel 14 need not necessarily have a cylindrical cross-section. The device 2 can also be equipped with a plurality of tubes connected to the outlet 10 via manifold, a single tube with a plurality of channels or any combination thereof. The cavity 6 can also be devised so that it induces gas passing downwardly through the container 4 to move in a helical whorl. In this instance, the tube 12 can also be devised in a similar manner. This would result in a longer heat-exchange distance without any increase in the external dimensions of the container.

The basic feature for the functioning of the device according to the invention is to utilize a thermal gradient between the flowing gas and the surroundings in order to first reduce the temperature of the flowing gas, without the need for any external sources of power (i.e., a passive device), in order to achieve condensation and then increase the temperature by utilizing the gas's own heat, thereby reducing the relative humidity of the flowing gas.

Although modifications and changes may be suggested by those skilled in the art, it is the intention of the inventors to embody within the patent warranted hereon all changes and modifications as reasonably and properly come within the scope of their contribution to the art.

We claim as our invention:

1. A device for reducing the relative humidity of a flowing gas, said flowing gas having a temperature warmer than ambient atmosphere in which said device is disposed, said device comprising:

a container having a top end and a bottom end with a cavity with an interior wall therebetween, and an inlet for flowing gas containing water vapor disposed at said top end;

an element consisting of heat conducting material having a through-channel therein disposed in said cavity of said container, said through-channel of said element having an opening disposed in said cavity spaced from said bottom end of said container, and having an opening forming an outlet for said flowing gas disposed at said top end of said container, said container and said element forming, in combination, means for dehumidifying and reducing the temperature of said flowing gas entering said container through said inlet by heat exchange between said flowing gas and an upper portion of said element for producing cooler flowing gas and thereby warming said upper portion of said element as said cooler flowing gas flows in a flow path from said top end of said container through said cavity to said bottom end of said container and into said through-channel and by condensing water, in said flow path, from said cooler flowing gas on said interior wall of said cavity, and by re-heating said cooler flowing gas exiting said container through the warmed upper portion of said through-channel and said outlet; and means for thermally insulating said element from said container.

2. A device as claimed in claim 1 wherein said element comprises a thin-walled tube.

3. A device as claimed in claim 1 wherein said container comprises a thin-walled container consisting of a heat-conducting material.

4. A device as claimed in claim 1 wherein said element has an exterior surface and carries means on said exterior surface for enlarging the area of said exterior surface.

5. A device as claimed in claim 4 wherein said means for enlarging the area of said exterior surface of said element comprises a plurality of projections extending from said element toward said container.

6. A device as claimed in claim 1 wherein said container has an exterior surface and carries means on said exterior surface for enlarging the area of said exterior surface.

7. A device as claimed in claim 6 wherein said means for enlarging the area of said exterior surface of said container comprises a plurality of projections extending from said exterior surface.

8. A device as claimed in claim 1 wherein said cavity has a cylindrical shape.

9. A device as claimed in claim 1 wherein said element and said through-channel each have a cylindrical shape.

10. A device as claimed in claim 9 wherein said element has an exterior with a screw-like flange thereon extending along a longitudinal length of said element and facing said container.

11. A device as claimed in claim 1 wherein said container has a tap hole at said bottom end, and said device further comprising a collection vessel detachably connected to an exterior of said container at said bottom end of said container for collecting liquid, condensed from said flowing gas, through said tap hole.

12. A device as claimed in claim 1 wherein said element comprises a further through-channel disposed in said cavity and communicating with said outlet.

13. A device as claimed in claim 1 further comprising a further element disposed in said cavity, said further element having a through-channel therein and said through-channel in said further element communicating with said outlet.

14. A device as claimed in claim 1 wherein said element comprises a plurality of longitudinally joined segments and means disposed between each segment for thermally separating adjacent segments.

* * * * *